US011338092B1

(12) United States Patent
Gadh

(10) Patent No.: US 11,338,092 B1
(45) Date of Patent: May 24, 2022

(54) ELECTRONICALLY REGULATED INJECTION PEN

(71) Applicant: Rundeep Gadh, Cooper City, FL (US)

(72) Inventor: Rundeep Gadh, Cooper City, FL (US)

( * ) Notice: Subject to any disclaimer, the term of this patent is extended or adjusted under 35 U.S.C. 154(b) by 317 days.

(21) Appl. No.: 16/016,287

(22) Filed: Jun. 22, 2018

Related U.S. Application Data

(60) Provisional application No. 62/528,380, filed on Jul. 3, 2017.

(51) Int. Cl.
| | | |
|---|---|---|
| *A61M 5/315* | (2006.01) | |
| *A61M 5/50* | (2006.01) | |
| *A61M 5/32* | (2006.01) | |
| *A61M 5/31* | (2006.01) | |

(52) U.S. Cl.
CPC .... *A61M 5/31546* (2013.01); *A61M 5/31583* (2013.01); *A61M 5/3202* (2013.01); *A61M 5/502* (2013.01); *A61M 2005/3126* (2013.01); *A61M 2005/31588* (2013.01); *A61M 2202/0484* (2013.01); *A61M 2205/3553* (2013.01); *A61M 2205/3584* (2013.01); *A61M 2205/50* (2013.01);
(Continued)

(58) Field of Classification Search
CPC ...... A61M 5/31546; A61M 2202/0484; A61M 5/3202; A61M 2005/3126; A61M 5/502; A61M 5/31583; A61M 2205/8206; A61M 2209/088; A61M 2205/3584; A61M 2205/50; A61M 2005/31588; A61M 2205/584; A61M 2205/3553; A61M 2005/2407; A61M 5/24; A61M 2005/2403; A61M 5/31565; G16H 40/63
See application file for complete search history.

(56) References Cited

U.S. PATENT DOCUMENTS

| | | |
|---|---|---|
| 7,169,133 B2 | 1/2007 | Broennimann et al. |
| 7,955,308 B2 | 6/2011 | Westbye |
| 7,976,509 B2 | 7/2011 | Moser et al. |

(Continued)

FOREIGN PATENT DOCUMENTS

| | | | |
|---|---|---|---|
| EP | 0749760 A2 * | 12/1996 | .......... A61M 5/3129 |
| EP | 3476417 A1 * | 10/2017 | |

(Continued)

OTHER PUBLICATIONS syndelasia.com, socorex injector.
fmb.com, vaccinators & injectors.
yds_ypsomed.com.

*Primary Examiner* — Amy R Weisberg
(74) *Attorney, Agent, or Firm* — H. John Rizvi; H. John Rizvi—The Patent Professor©

(57) ABSTRACT

An injection pen to deliver a predefined dose of substance according to a prescribed schedule is disclosed. The injection pen includes a first portion having a medicinal chamber and a removable cover. The medicinal chamber is coupled to a piston on one end and attachable to an injection needle on an opposite end. The removable cover includes a solution dispenser. The injection pen includes a second portion couplable to the first portion. The second portion includes an actuator coupled to the piston for actuating the piston in an injection. The actuator may be controlled by an electronic circuit board embedded within the injection pen to regulate the delivery of a substance in the medicinal chamber based on a prescribed dose and injection schedule.

10 Claims, 8 Drawing Sheets

(52) U.S. Cl.
CPC ................. *A61M 2205/584* (2013.01); *A61M 2205/8206* (2013.01); *A61M 2209/088* (2013.01)

(56) References Cited

U.S. PATENT DOCUMENTS

| | | | | |
|---|---|---|---|---|
| 8,353,878 | B2 * | 1/2013 | Moller | A61M 5/31533 604/207 |
| 8,412,310 | B2 | 4/2013 | Liu et al. | |
| 9,700,710 | B2 * | 7/2017 | Anderson | A61M 39/20 |
| 2003/0229308 | A1 * | 12/2003 | Tsals | A61M 5/20 604/116 |
| 2005/0171476 | A1 * | 8/2005 | Judson | A61M 5/20 604/131 |
| 2007/0225656 | A1 | 9/2007 | Hoyle, Jr. | |
| 2009/0312695 | A1 * | 12/2009 | Wilson | A61M 5/1723 604/31 |
| 2010/0114025 | A1 | 5/2010 | Moller | |
| 2010/0185152 | A1 * | 7/2010 | Larsen | A61M 5/20 604/154 |
| 2011/0054440 | A1 * | 3/2011 | Lewis | A61M 39/20 604/506 |
| 2012/0165620 | A1 * | 6/2012 | Tanis | G16H 40/63 600/301 |
| 2014/0148781 | A1 * | 5/2014 | Tekeste | A61M 39/0247 604/506 |
| 2014/0227144 | A1 * | 8/2014 | Liu | A61L 2/16 422/300 |
| 2017/0157340 | A1 * | 6/2017 | Moeller | A61M 5/24 |
| 2017/0216524 | A1 * | 8/2017 | Haider | A61M 5/1723 |
| 2019/0015598 | A1 * | 1/2019 | Takemoto | A61J 1/14 |
| 2019/0091406 | A1 * | 3/2019 | Okamura | A61M 5/31546 |
| 2019/0240394 | A1 * | 8/2019 | Horvath | A61M 5/1785 |
| 2020/0094024 | A1 * | 3/2020 | Teoh | A61M 25/0618 |

FOREIGN PATENT DOCUMENTS

| | | | | |
|---|---|---|---|---|
| WO | WO-2004014469 | A1 * | 2/2004 | ............ A61L 2/00 |
| WO | WO-2010098931 | A * | 1/2010 | |
| WO | WO-2013076026 | A1 * | 11/2012 | |
| WO | WO-2015124923 | A1 * | 2/2015 | |

* cited by examiner

ELECTRONICALLY REGULATED INJECTION PEN

CROSS-REFERENCE TO RELATED APPLICATION

This application claims the benefit of U.S. Provisional Patent Application Ser. No. 62/528,380, filed Jul. 3, 2017, which is incorporated herein in its entirety.

FIELD OF THE INVENTION

The present invention relates generally to medical devices for medical substance delivery, and more particularly, to an injection pen for delivering a limited dose of a substance.

BACKGROUND OF THE INVENTION

Injection pens are medical devices used for delivering medical substances and medications to a patient under supervision of a doctor or a pharmacist at a clinic. For injecting allergy medications, patients may visit a clinic as per a fixed schedule. In some cases, to avoid visiting a clinic every time for receiving a medication or a substance, patients may use injection pens, filled with a prescribed substance or medication, on their own for convenience and ease.

There are some substances, for instance allergy medications, which are required to be delivered in correct dosage, as an overdose of such substances may cause subsequent reactions and life-threatening conditions. Additionally, allergy substances are to be delivered strictly as per a predefined schedule, such as once or twice a week, as prescribed by a doctor. Using an injection pen, patients may be prescribed to inject a substance manually at home or on their own as per a schedule prescribed by a doctor.

However, patients must manually use injection pens, and this may cause over dose or untimely delivery of a substance leading to compliance and health issues. Further, patients may accidentally inject a wrong substance, or medication.

As such, there exists a need for an injection pen that allows patients to deliver substances with convenience and to prevent any unwanted consequences due to excess dosage or untimely delivery of a substance.

SUMMARY OF THE INVENTION

This summary is provided to introduce a selection of concepts in a simplified form that are further described below in the detailed description. This summary is not intended to identify key features or essential features of the claimed subject matter, nor is it intended to be used to limit the scope of the claimed subject matter. Furthermore, the claimed subject matter is not limited to embodiments that solve any or all disadvantages noted in any part of this disclosure.

According to embodiments of the present disclosure, an injection pen for injecting a substance of a predefined dose to a patient body is disclosed. The injection pen is a medical device including a first portion and a second portion. The second portion is detachably coupled to the first portion through a coupling configuration. The first portion may include a medicinal chamber which is covered and surrounded partially by a removable cover. The medicinal chamber may be coupled to a piston on a first end (i.e. proximal end) and may be coupled to an injection needle on an opposite second end (e.g. distal end). The piston may be coupled to the medicinal chamber and an actuator such that the piston may slide within the medicinal chamber for a defined sliding length. A solution dispenser is located on the first portion and configured to dispense a solution on the patient body for safely injecting or inserting the injection needle.

The second portion includes an actuator coupled to the piston and the medicinal chamber. In an example, the actuator may regulate delivery of a substance from the medicinal chamber to the injection needle and may be controlled by an electronic circuit board embedded within the injection pen. The electronic circuit board regulates delivering a substance based on a predefined dose and a predefined schedule.

In another aspect, the second portion includes a knob at the proximal end where the knob is coupled to the piston to cause the piston to slide within the medicinal chamber when the knob is actuated.

In another aspect, the second portion includes a display panel to display at least one of a predefined dosage of a substance, time to apply a next dose, battery status, and a Bluetooth signal indicator.

In another aspect, the injection pen is communicatively coupled to a user device through a short-range wireless connection, and the user device is connected to a remote device through a wireless or wired network.

Further disclosed is an injection pen for injecting a substance of a predefined dose to a patient body, the injection pen comprising, a medicinal chamber configured to store an injectable substance, a piston coupled to the medicinal chamber, such that actuating the piston forces the injectable substance out of the medicinal chamber, and an electronic circuit configured to control actuation of the piston.

In another aspect, the electronic circuit is configured to control actuation of the piston such that the predefined dose of the injectable substance is dispensed from the medicinal chamber.

In another aspect, the electronic circuit is configured to control actuation of the piston such that the predefined dose of the injectable substance is dispensed from the medicinal chamber according to a predefined schedule.

In another aspect the injection pen further comprises a programmable port, wherein the electronic circuit is programmed with one or both of the predefined dose and the predefined schedule by a remote device coupled to the programmable port.

In another aspect, the electronic circuit is configured to lock the piston in response to improper use of the injection pen.

In another aspect, the electronic circuit is configured to unlock the piston in response to receiving a pass code from a remote device.

In another aspect, the injection pen further comprises a display panel configured to display information related to one or more of a predefined dose of the injectable substance, a predefined schedule of the injectable substance, a battery status of the injection pen, and a network connection status.

In another aspect, the injection pen further comprises a battery configured to supply power to the electronic circuit, and a charging terminal including an interface configured to couple with a power source.

In another aspect, the injection pen further comprises a knob, wherein the electronic circuit is configured to control actuation of the piston in response to actuation of the knob.

Further disclosed is an injection pen, comprising: a removable cover, a medicinal chamber configured to store an injectable substance, the medicinal chamber being exposed upon removal of the removable cover, a piston slidably coupled to the medicinal chamber and configured to expel the injectable substance upon actuation, and a controller configured to: receive a predefined dose, receive a predefined schedule, and selectively actuate the piston based on the predefined dose and the predefined schedule to thereby dispense the predefined dose of the injectable substance according to the predefined schedule.

In another aspect, the medicinal chamber includes an attachment portion configured to receive an injection needle with which the injectable substance is administered to a user body.

In another aspect, the removable cover includes, a solution chamber configured to store a solution, and a solution dispenser at a distal end, the solution dispenser configured to selectively dispense the solution from the solution chamber.

In another aspect, the solution includes an alcohol-based solution that prepares an injection site on a user body for injecting the injectable substance.

In another aspect, the injection pen further comprises a knob, wherein the controller is configured to selectively actuate the piston based further on actuation of the knob.

In another aspect, the controller is configured to lock actuation of the piston in response to improper use of the injection pen.

In another aspect, after locking actuation of the piston, the controller is configured to unlock actuation of the piston in response to receiving a pass code.

Further disclosed is an injection pen for injecting a substance of a predefined dose to a patient body, the injection pen comprising, a first portion including a removable cover, a second portion removably coupled to the first portion, a medicinal chamber configured to store an injectable substance, the medicinal chamber being exposed upon removal of the removable cover, a piston coupled to the medicinal chamber, such that actuating the piston forces the injectable substance out of the medicinal chamber, and an electronic circuit configured to actuate the piston in response to detecting a condition.

In another aspect, the condition includes actuation of a knob of the injection pen.

In another aspect, the condition includes a predefined dose of the injectable substance being available in the medicinal chamber.

In another aspect, the condition includes the piston being unlocked.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the claimed subject matter will hereinafter be described in conjunction with the appended drawings provided to illustrate and not to limit the scope of the claimed subject matter, where like designations denote like elements, and in which:

It is to be understood that like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any embodiment described herein as "exemplary" or "illustrative" is not necessarily to be construed as preferred or advantageous over other embodiments. All of the embodiments described below are exemplary embodiments provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
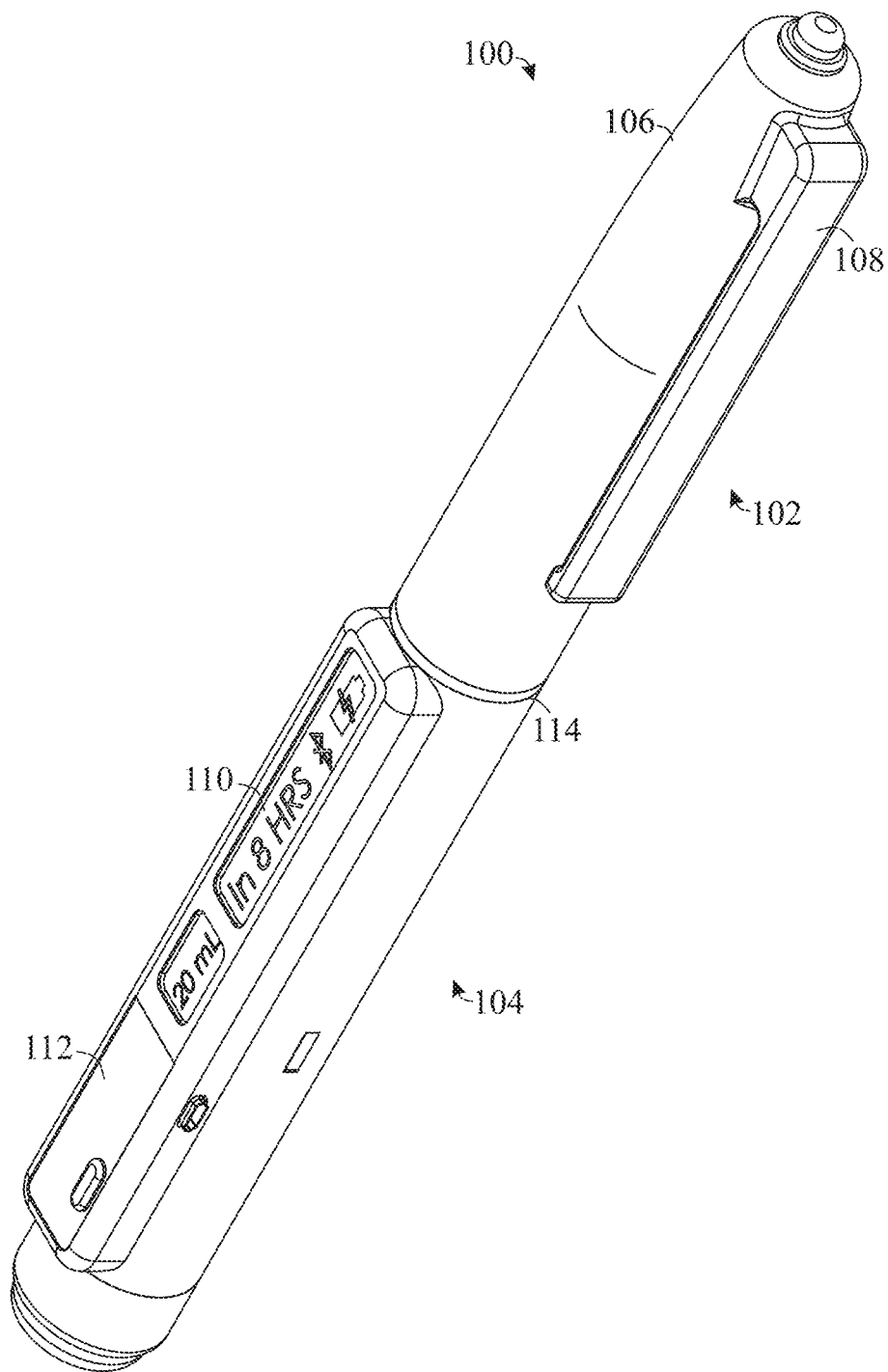
FIGS. 1 and 2 present perspective views of an injection pen in accordance with aspects of the present disclosure.
Figure 2:
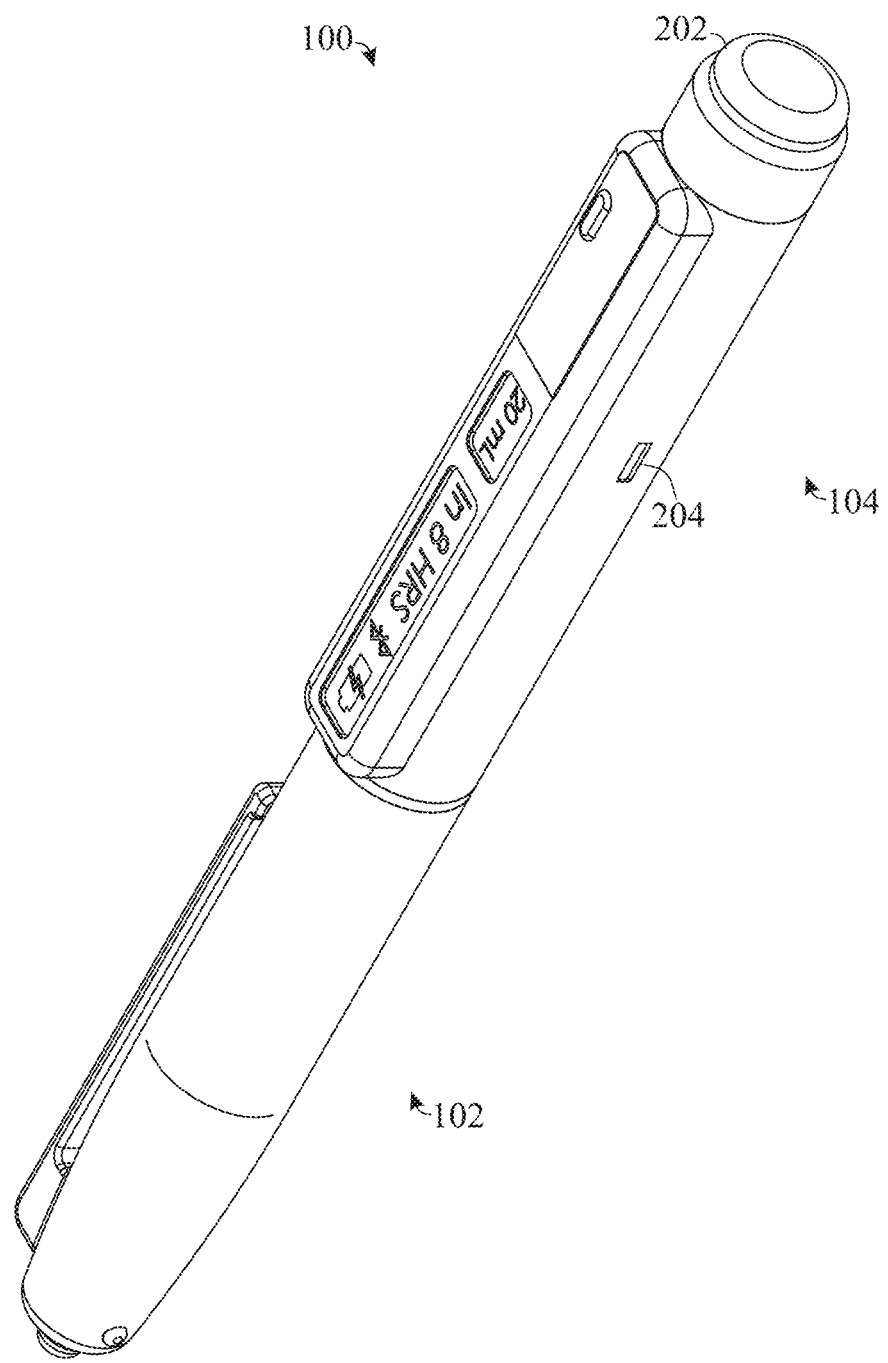

The illustrations of FIGS. 1 and 2 present perspective views of an injection pen that cures the problems and issues presented in the background description above. The injection pen 100 may be a portable medical device that allows patients to safely deliver substances and medications in predefined amounts with ease and convenience as prescribed by a doctor, by regulating allowable or authorized dosage volumes and application times.

Figure 3:
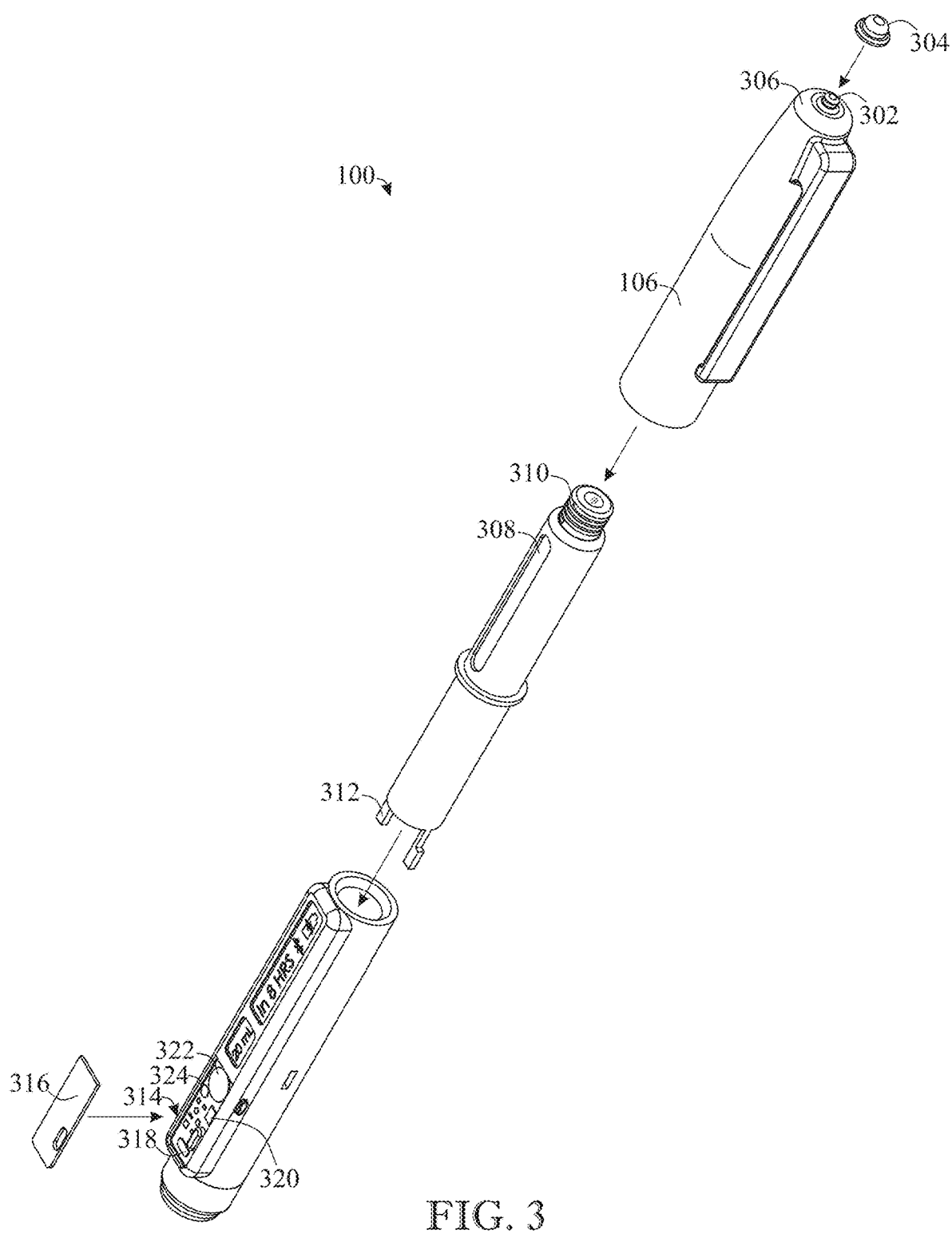
FIG. 3 presents an exploded view of the injection pen in accordance with aspects of the present disclosure.

The injection pen 100 as shown in FIG. 1 includes a first portion 102 and a second portion 104. The second portion 104 is couplable to the first portion 102 via locking tabs 312 as shown in FIG. 3. In one example, the injection pen 100 is composed of a plastic material or a light metal, or a combination thereof.

Figure 4:
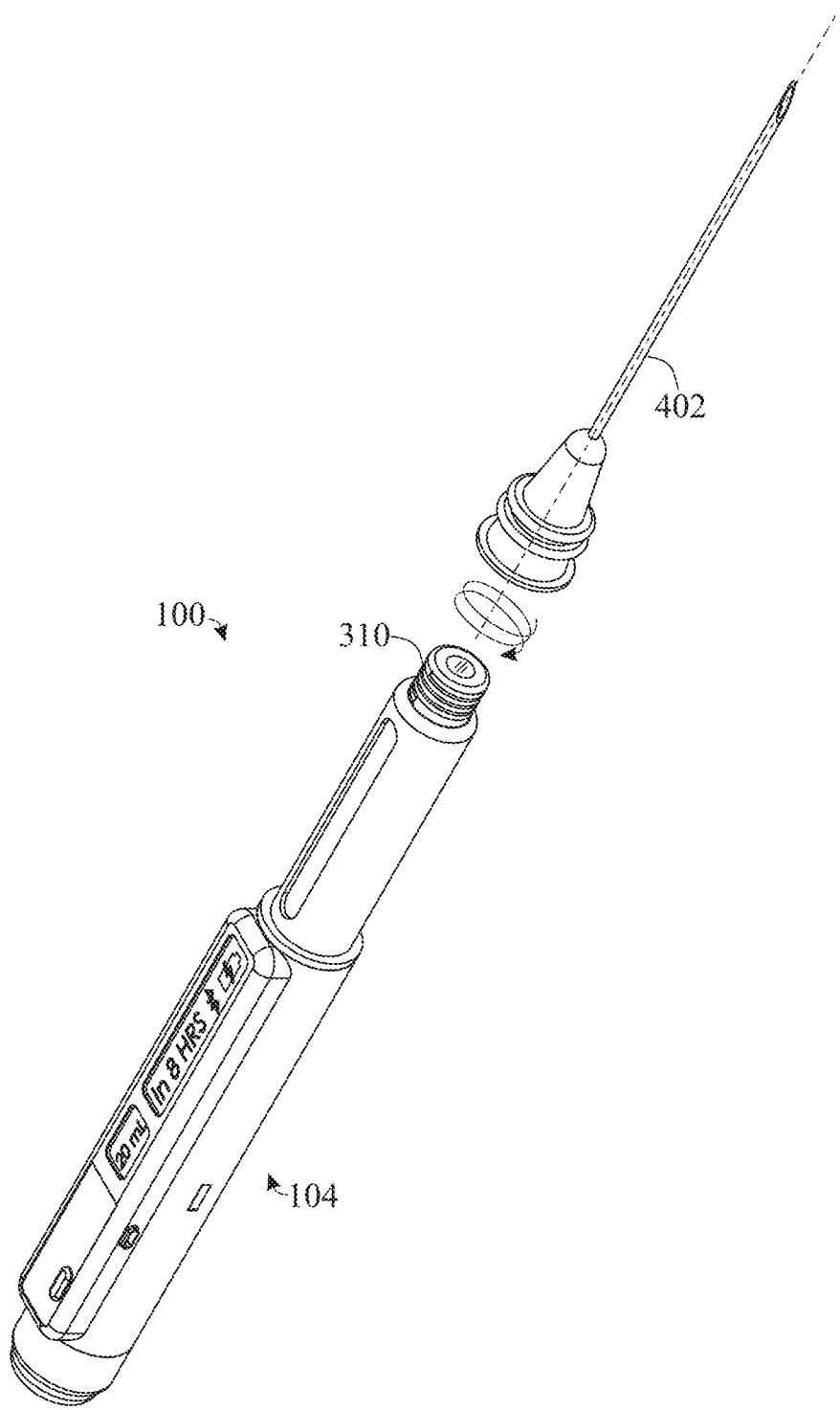
FIG. 4 presents a perspective view of an injection needle being coupled to the injection pen in accordance with aspects of the present disclosure.
Figure 5:
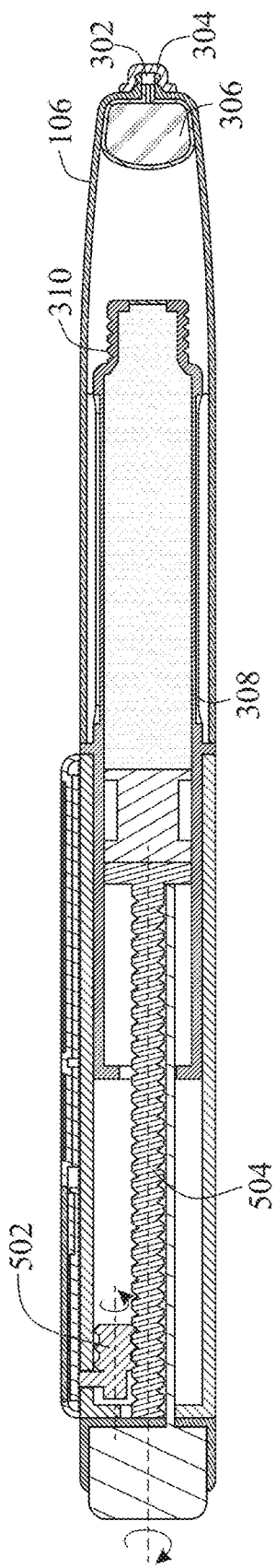
FIGS. 5 and 6 present longitudinal cross-sectional views of the injection pen in various configurations, in accordance with aspects of the present disclosure.

The first portion 102 includes a removable cover 106 and a medicinal chamber 308. The removable cover 106 includes a clip 108 for clipping to a pocket of a shirt or trousers to enhance convenience and portability. The removable cover 106 covers the medicinal chamber 308 completely or partially when the medicinal chamber 308 is attached to the second portion, and the removable cover 106 is attached over the medicinal chamber 308. For example, FIG. 5 shows the cover 106 in an attached configuration covering the medicinal chamber 308. The medicinal chamber 308 may include an attachment portion 310 on a distal end of the medicinal chamber 308 and a pair of locking tabs 312 on the a proximal end of the medicinal chamber. In one example, the attachment portion 310 may be one of a threaded portion or a luer connector, as shown in FIG. 3, to couple to an injection needle 402 as shown in FIG. 4. The pair of locking tabs 312 at the proximal end of the medicinal chamber 308 may be configured to be a coupling configuration for coupling the first portion 102 and the medicinal chamber 308 to the second portion 104. Between the first portion 102 and the second portion 104 a color-coded ring 114 may be located. For example, the color coded ring 114 may be located on a distal end of the first portion 102, or a proximal end of the second portion 104. In some examples the cover may be configured to cover both the medicinal chamber 308 and the needle 402 while the needle is attached to the medicinal chamber 308.

Figure 6:
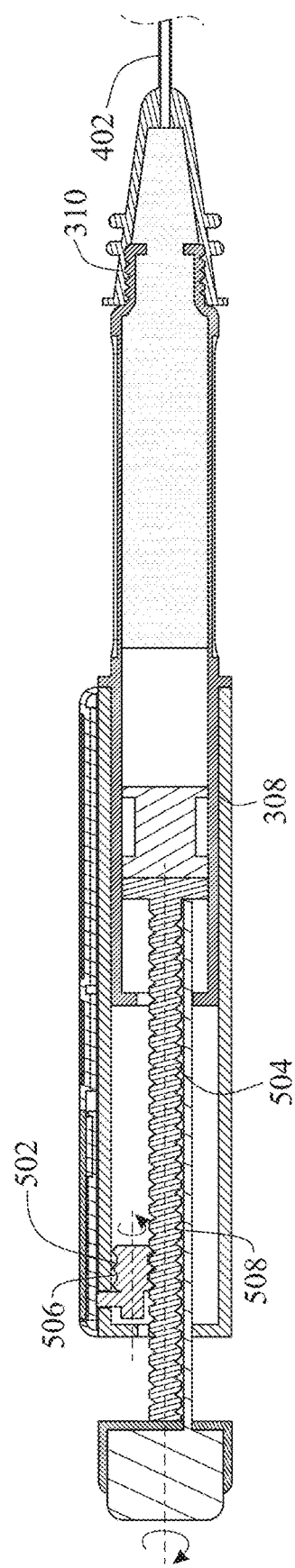
Figure 7:
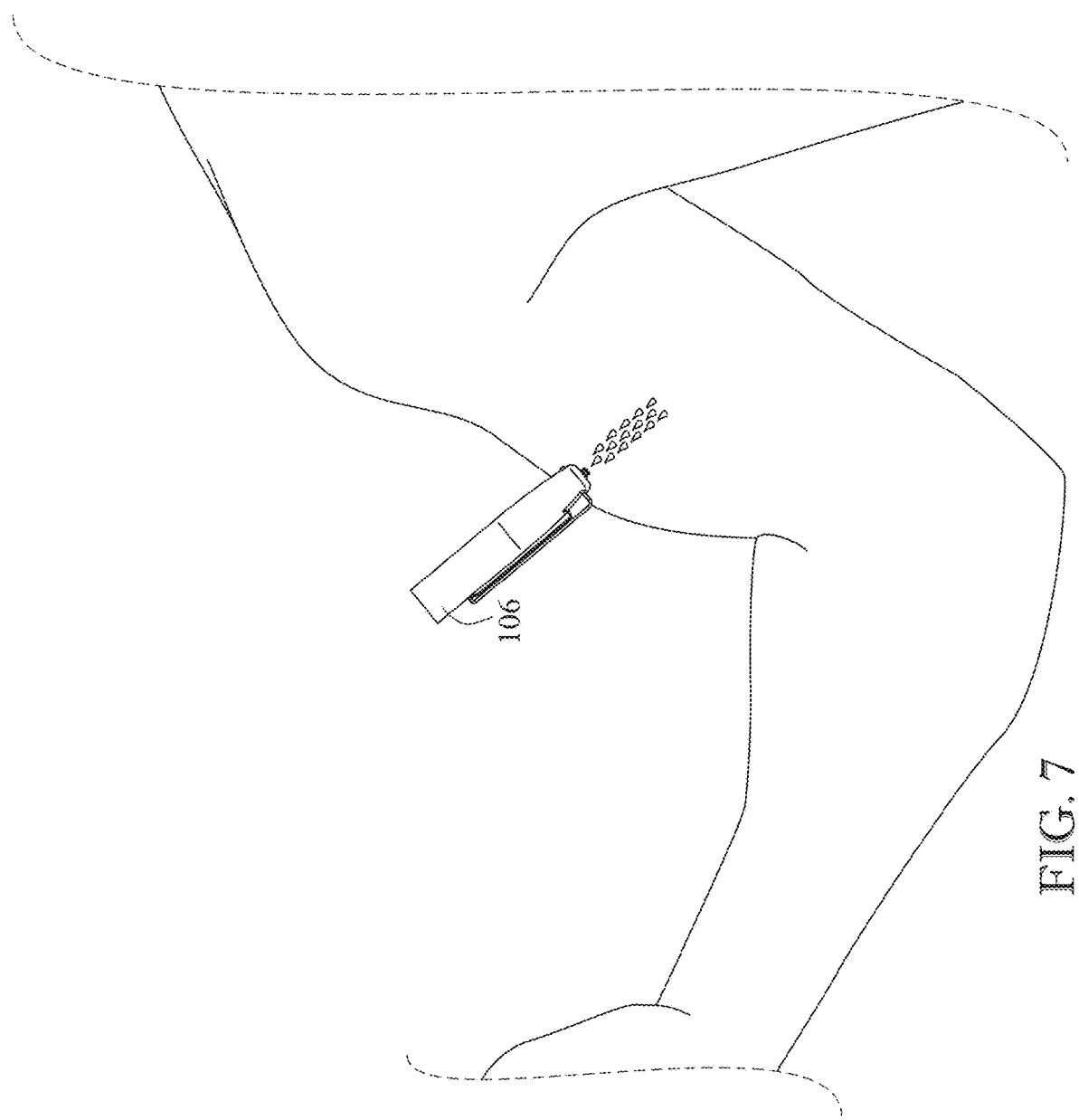
FIG. 7 schematically presents the injection pen dispensing a preparation solution to a patient arm surface, in accordance with aspects of the present disclosure.

The illustration of FIG. 4 shows the injection needle 402 being coupled to a distal end of the medicinal chamber 308 via the attachment portion 310, after the removable cover 106 has been removed. As shown in the FIG. 4, the injection needle 402 is being threadedly engaged with the attachment portion 310. In one example, the injection needle 402 may be rotated in a predefined direction to threadedly engage with the attachment portion 310 of the injection pen 100. The injection needle 402 may be engaged such that a substance stored in the medicinal chamber 308 may flow through the injection needle 402, through a tip of the injection needle 402. In other words, the injection needle 402 may be coupled such that the medicinal chamber 308 is fluidly coupled to the injection needle 402 and a substance stored in the medicinal chamber may flow through the medicinal chamber 308 through the injection needle 402 through a distal aperture of the needle 402, for delivery of a substance stored inside the medicinal chamber 308. For example, FIG. 6 shows the needle having been fully attached or coupled to a distal portion of the medicinal compartment 308.

The medicinal chamber 308 may be configured to store a substance or medication as filled by a doctor or a pharmacist at a clinic or pharmacy, based on a dosage prescription and/or prescription schedule. For example, a prescription schedule may indicate a frequency of injection for a substance, or exact times or days a substance needs to be injected. A dosage prescription may define a dosage volume per application of a substance stored in the medicinal chamber 308.

Figure 8:
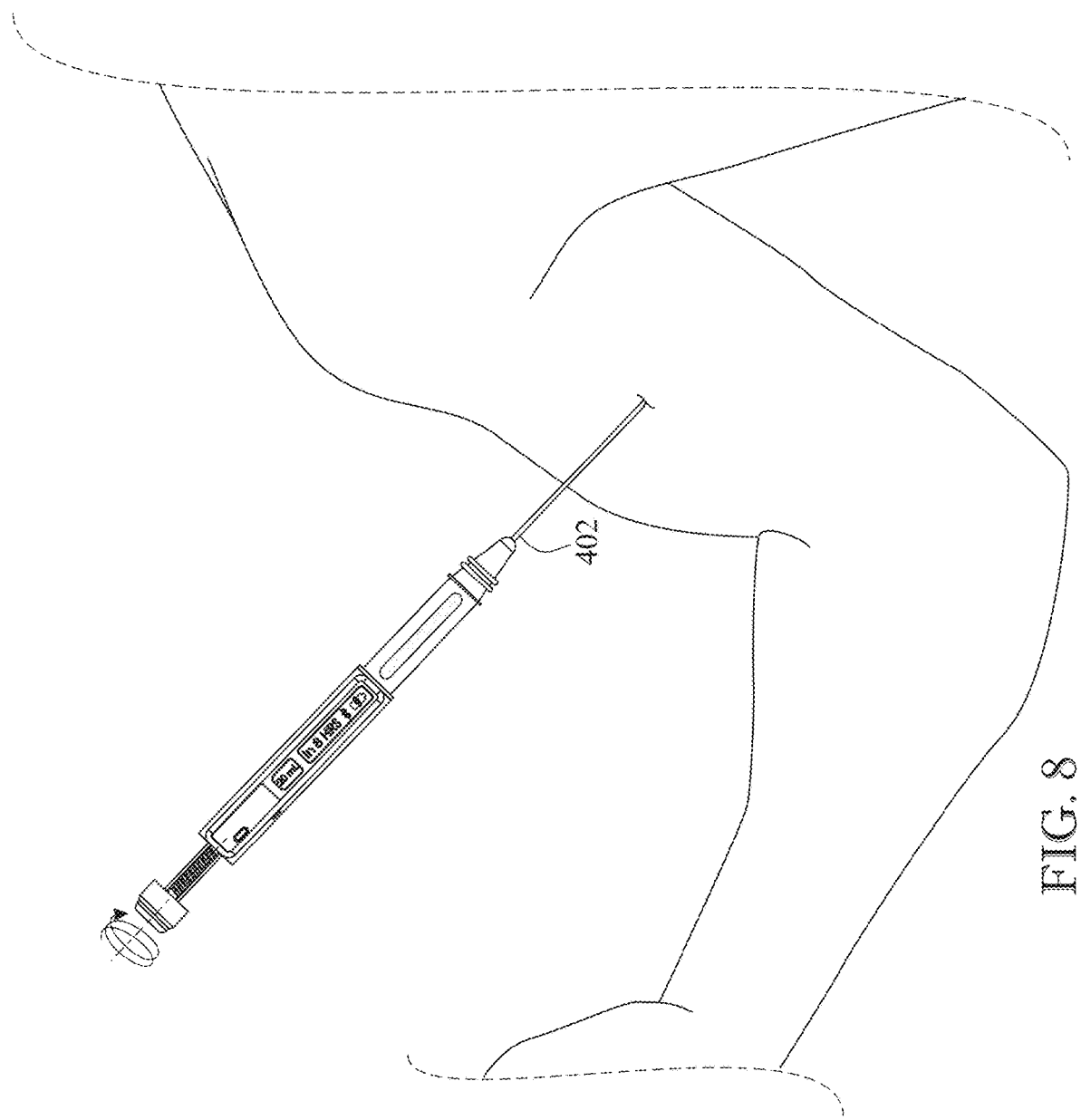
FIG. 8 schematically presents the injection pen injecting a substance into a patient arm, in accordance with aspects of the present disclosure.

The illustration of FIG. 3 illustrates an exploded view of the injection pen 100 where the removable cover 106 includes a solution dispenser 302 on a distal end of the removable cover 106 for dispensing a solution. In one example, the solution may be an alcohol based solution, for instance isopropyl alcohol or ethanol, to prepare an injection site on a patient's body. The solution dispenser 302 may have an opening to dispense the solution and may include a dispenser cover 304. The removable cover 106 may include a solution chamber 306 to store the solution. The solution dispenser 302 may be fitted on the removable cover 106 such that the solution dispenser 302 is coupled to the solution chamber 306 to receive the solution from the solution chamber 306 and dispense the solution to a patient body for preparing a portion of the patient body for injection as schematically shown in FIG. 8. For example as shown in FIG. 5, the removable cover 106 is in an attached configuration at a distal end of the injection pen 100, the cover 106 including the solution dispenser 302, the dispenser cover 304 (e.g. cap), and the solution chamber 306. Therefore, the injection pen 100, and more particularly the dispenser 302, may be utilized for spraying or dispensing a preparation solution on a patient body to prepare an area of the body for injection. The dispenser 302 may include a brush to brush or swab the solution on the patient's skin. The dispenser cover 304 may be a cap that may be first removed before swabbing the preparation solution of the dispenser 302 on a patient's skin.

The second portion 104 may include an electronic circuit board 314 and a circuit cover 316 placed on the electronic circuit board 314 for covering the circuit board 314. The second portion 104 may further include a display panel 110. The display panel 110 may be a rectangular LCD panel to display information related to a predefined dose (e.g. dosage volume in mL), a schedule in terms of hours or minutes (or any time period) for applying a next dose, a battery status of the pen 100, and a network connection status (e.g., a Bluetooth connection indicator). As shown in FIG. 3, the electronic circuit board 314 includes a programmable port 318, a Bluetooth transmitter 320, a battery 322, and a backup battery 324. Such a programming port may be connected to a device of a medical professional to allow the medical professional to program the electronic circuit board 314 of the pen 100 for regulating, blocking, allowing, or authorizing dosage volumes and/or application times. The electronic circuit board 314 may include a suitable controller (e.g., processor, system-on-a-chip, other suitable logic device) configured to implement the approaches described herein, including actuation of piston 504 according to predefined dosages and/or predefined schedules, unlocking or locking based on authorized or unauthorized use of the pen 100, etc.

The Bluetooth transmitter 320 may be used for connecting the injection pen 100 to a user device such as a smart phone through short-range Radio Frequency (RF) communication. Any appropriate wireless or wired networking system may be employed to wirelessly connect the pen 100 to a user device, or a medical professional device.

The second portion 104 may include a charging terminal 204 for charging a battery 322. The charging terminal 204 may include any suitable interface configured to couple with a power source and enable charging of battery 322, including but not limited to a universal serial bus (USB) interface. The battery 322 may be a chargeable battery to supply power to the electronic circuit board 314 and the display panel 110, and the backup battery 324 may be automatically activated to supply power to the electronic circuit board 314 and the display panel 110 when the battery 322 is about to discharge or run out of stored energy.

Figure 9:
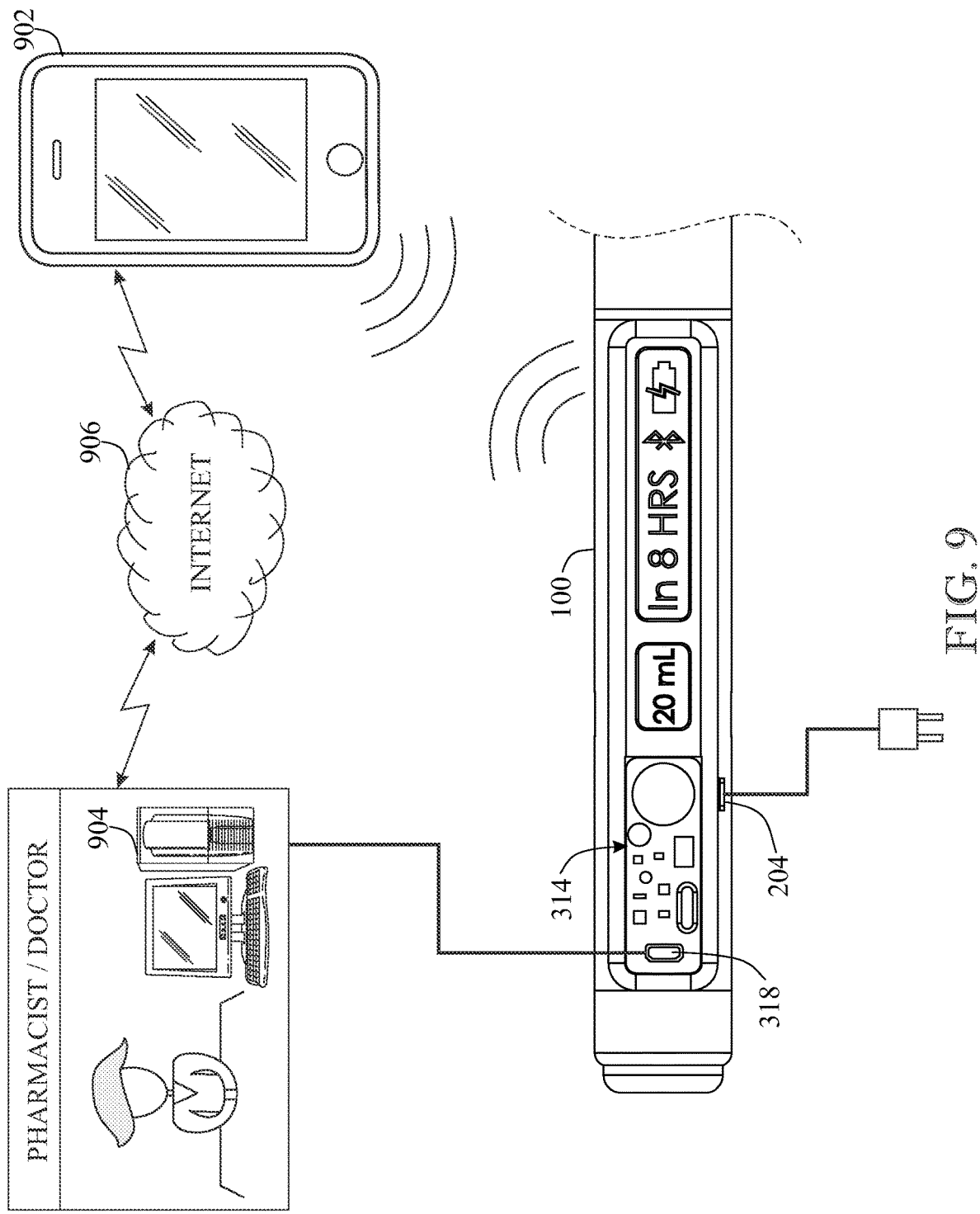
FIG. 9 schematically presents a network environment, where the injection pen is connected to a user device in accordance with aspects of the present disclosure.

As mentioned above, the programmable port 318 may be used to program the electronic circuit board 314 for automatically regulating (e.g. allowing or blocking) authorized or unauthorized outflow of a substance from or in the medicinal chamber 308 based on a predefined prescribed dose and a predefined prescribed schedule prescribed by a doctor. For example, as shown in FIG. 9, a pharmacist or doctor user may connect a computing device 904 to the programmable port 318 to program the electronic circuit board 314 according to a predefined dose or predefined schedule. To enable this feature, the electronic circuit board 314 of the injection pen 100 may be programmed to control an actuator 502 such that the actuator regulates delivery of a substance in the medicinal chamber for a predefined dose for each injection as per a predefined schedule. As shown in FIGS. 5 and 6, a piston 504 may be slidably coupled to the medicinal chamber 308 such that the piston may slide within the medicinal chamber 308 according to an actuation applied by the actuator 502 and the electronic circuit.

The electronic circuit board 314 may be configured to lock the piston 504 in place, and/or lock the actuator 502, or regulate a distance the piston 504 may travel in the medicinal chamber 308, according to the prescribed schedule and/or dosage volume uploaded, downloaded, or configured by a doctor user through the programmable port 318, such that a patient user may only be allowed inject a substance as prescribed by a doctor. For example, attempts to administer a substance using the pen 100, that are not exactly following a doctor's prescription, may be detected by the electronic circuit board 314 as being unauthorized. Unauthorized attempts may be automatically blocked or locked by the electronic circuit board 314 by locking or limiting motion of actuator 502 and/or piston 504. Thus, the injection pen 100 includes a safety feature of preventing the actuator from actuating the piston 504 unless a dosage is due according to the predefined schedule, and/or a preceding dosage has been correctly and timely applied. The circuit board 314 may lock the actuator permanently if the pen 100 is used improperly— e.g., if the dosage is not used properly in a designated time frame/not in accordance with the predefined schedule, an attempt to inject an amount other than the predefined dosage is made, and/or a dosage is incorrectly used. For example, FIGS. 5 and 6 show the actuator 502 being coupled to the piston 504. Thus, the actuator 502 may be controlled by the electronic circuit board 314 to control movement of the piston 504 and regulate delivery of a substance as per a predefined dose or schedule.

As a non-limiting example, the actuator may include one or more motorized components that are configured to drive the piston 504. For example, the piston 504 may include a helical or screw-like structure that engages with the actuator such that the actuator rotates the piston 504 for driving the piston longitudinally in the medicinal chamber 308. The electronic circuit board 314, the actuator 502, and/or the piston 504 may be calibrated such that an exact or accurate prescribed dosage is applied in an injection when the actuator is actuated. For example, a rotation rate, torque, or angular velocity of the piston may be calibrated with the actuator and/or the circuit board for delivering an exact dosage according to a prescribed schedule and dosage volume programmed by a medical professional user. As shown in FIG. 8, the actuator 502 may include a helical thread 506 that is configured to engage with a helical thread 508 of the piston 504, such that rotating the actuator may rotatably drive the piston 504 to cause the piston 504 to push a substance out of the medicinal chamber 308 as shown in FIG. 8.

The illustration of FIG. 2 shows the second portion 104 of the injection pen 100 including a knob 202 on a proximal end. The knob may be configured such that, to deliver a substance or actuate the actuator, a patient may press or activate the knob 202 as shown in FIG. 8. The knob 202 may include a rotatable portion that rotates when a substance is being dispensed from the medicinal chamber, and/or a push button to cause the substance to be dispensed and administered. Rotatable portions of the knob may be fixed to the piston. The knob 202 may be operatively connected directly or indirectly to the electronic circuit board for actuating the actuator 502 upon the knob 202 being actuated, actuated, or pressed.

The pen 100 may automatically advance a dosage volume by 0.05 mL after each injection. For example, a first injection volume may be 0.05 mL, a second injection volume may be 0.10 mL, and a third injection volume may be 0.15 mL. Each properly applied dose may automatically mark a calendar indicating that a prescribed dose was properly injected. The medicinal chamber 308 may be refilled by a doctor or medical professional with increasingly concentrated allergy medications according to a doctor's prescription. For example, after the pen 100 has determined that 10 shots have been properly administered, the pen may be unlocked and refilled by a medical professional. Refilling the pen 100 may be accomplished by inserting a pre-filled vial or injecting a substance into the medicinal chamber 308. For example, such vials may be 5 ml vials, and the vials may have varying concentrations. It is to be understood that an injectable substance may include antibiotics or steroids. A dosage volume may be any appropriate dosage volume and an injection frequency may be any appropriate injection frequency according to a prescribed medication. As a non-limiting example, the rotatable knob 202 may be or may include a dosage dial that a medical professional may rotate or use to set a correct volume of a dose. Further, a medical professional may unlock the pen to open up and refill the pen, as described herein. Unlocking the pen 100 may allow a medical professional to replace the medicinal chamber 308 to refill the pen 100. For example, unlocking the pen may allow one or more parts of the pen to be disassembled for accessing and/or replacing the medical chamber 308.

The illustration of FIG. 9 schematically presents a network environment 900 comprising the injection pen in accordance with aspects of the present disclosure. The injection pen 100 is connected to a user device 902 through a short-range wireless connection. In an example, the user device 902 may be a smartphone, a laptop, or a desktop, and the short-range wireless connection may be a Bluetooth connection or a Near Field Communication (NFC) connection. Further, the user device 902 and the injection pen 100 may be connected to a remote device 904 at the doctor's clinic through a wireless or wired internet network 906. The remote device 904 may be a smartphone, a desktop, or a laptop, as non-limiting examples, and the wireless network 906 may be a private or a public network. The doctor may change the predefined dosage or the predefined schedule of the substance to be delivered to the patient by communicating with the electronic circuitry in the injection pen wirelessly or wiredly, or by communicating with a user device 902. For example, an updated schedule or updated prescription may be transferred from the remote device 904 to the user device 902 and/or the injection pen 100. The user device 902 may transmit the updated prescribed dosage or schedule to the injection pen 100. Based on the updated dosage or predefined schedule, the electronic circuit board 314 may be reprogrammed to control the actuator for delivering the substance. The injection pen 100 may be locked if the dosage was not taken as per a predefined schedule prescribed by a medical professional. In this scenario, the user device 902 may receive a pass code from the remote device 904, and the pass code may be transferred from the user device 902 to the injection pen 100 for unlocking the injection pen 100. In some embodiments, a pharmacist or doctor device 904 may directly send the pass code or an updated prescription or schedule to the injection pen. This may prevent the injection pen from being tampered with.

An electronic circuit of the injection pen 100 may actuate the piston 504 to thereby dispense an injectable substance stored in the medicinal chamber 308 in response to detecting a condition. In view of the above, the condition may include a variety of suitable criteria. For example, the condition may include the electronic circuit being configured with a predefined dosage at which to dispense the injectable substance (and potentially at least the predefined dosage being available and/or an attempt to dispense the injectable substance being in accordance with the predefined dosage), the electronic circuit being configured with a predefined schedule and an attempt to dispense the injectable substance being at a time in accordance with the predefined schedule, the piston 504 being unlocked, and/or detecting actuation of the knob 202. As the dispensation of an injectable substance, as well as the dispensation of a solution (e.g., in response to actuation of removal of dispenser cover 304), may be conditional in these ways, the injection pen 100 may selectively dispense the injectable substance and/or solution. As used herein, the "electronic circuit" of the injection pen 100 may refer to one or more electronic components used to implement the functions of the injection pen described herein, where the electronic component(s) may include one or more of the electronic circuit board 314, a controller or other logic machine, a storage machine, the programmable port 318, the Bluetooth transmitter 320, the battery 322, and the backup battery 324.

It is to be understood that any appropriate substance may be dispensed via the herein disclosed pen. In some embodiments the pen may be configured to dispense pills, according to a doctor's prescription, and according to programmable electronic circuitry of the pen. For example, the circuitry may be programmed to dispense one or more pills at certain times according to a prescription. Such an embodiment may aid in eliminating overdose or addiction to pills such as prescription opioids.

In conclusion, provided is a dosage limited injection pen that provides a fixed dose of a substance to a patient and allows timely delivery of the substance as per a prescribed schedule and/or dosage. The injection pen is configured such that substances or medications contained within the injection pen may only be refilled by a doctor, a pharmacist, or any appropriate licensed medical professional, thereby preventing tampering of the injection pen and medications contained in the injection pen. The injection pen may be locked until a prescribed time of delivery of the substance. Therefore, the injection pen provides convenience and safety to patients who need to take prescribed substances and medications on their own.

In some embodiments the methods, tasks, processes, and/or operations described above may be effected, executed, actualized, and/or carried out by a computing system including a tangible computer-readable storage medium, also described herein as a storage machine, that holds machine-readable instructions executable by a logic machine (i.e. a processor or programmable control device) to effect, execute, actualize, carry out, provide, implement, perform, and/or enact the above described methods, processes, operations, and/or tasks. When such methods, operations, and/or processes are implemented, the state of the storage machine may be changed to hold different data. For example, the storage machine may include memory devices such as various hard disk drives, CD, or DVD devices. The logic machine may execute machine-readable instructions via one or more physical information and/or logic processing devices. For example, the logic machine may be configured to execute instructions to perform tasks for a computer program. The logic machine may include one or more processors to execute the machine-readable instructions. The computing system may include a display subsystem to display a graphical user interface (GUI) or any visual element of the methods or processes described above. For example, the display subsystem, storage machine, and logic machine may be integrated such that the above method may be executed while visual elements of the disclosed system and/or method are displayed on a display screen for user consumption. The computing system may include an input subsystem that receives user input. The input subsystem may be configured to connect to and receive input from devices such as a mouse, keyboard or gaming controller. For example, a user input may indicate a request that a certain task is to be executed by the computing system, such as requesting the computing system to display any of the above described information, or requesting that the user input updates or modifies existing stored information for processing. A communication subsystem may allow the methods described above to be executed or provided over a computer network. For example, the communication subsystem may be configured to enable the computing system to communicate with a plurality of personal computing devices. The communication subsystem may include wired and/or wireless communication devices to facilitate networked communication. As non-limiting examples, the communication subsystem may include a global positioning system (GPS) module that includes one or more GPS receivers for determining a location of one or more electronic devices (e.g. a smart phone). The described methods or processes may be executed, provided, or implemented for a user or one or more computing devices via a computer-program product such as via an application programming interface (API).

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An injection pen for injecting a substance of a predefined dose to a patient, the injection pen comprising:
    a medical chamber substantially cylindrically shaped comprising at least one sidewall extending from an open distal end to a substantially closed proximal end, and defining an internal cavity, the medical chamber including a pair of coupling tabs extending outwardly from a distal peripheral edge of the distal end of the sidewall;
    a medical vial insertable into the internal cavity of the medical chamber through the open distal end;
    a needle selectively attachable to the closed proximal end of the medical chamber;
    a removable cap defining an internal space;
    a reservoir disposed inside of the internal space of the removable cap for storing a dispensable solution,
        wherein the dispensable solution is dispensed through a dispensing opening included on the reservoir that is disposed in the removable cap;
    a piston housing comprising at least one sidewall extending from a proximal open end and a substantially closed distal end, the piston housing having an interior cavity, and a pair of retaining slots in the interior cavity;
    an electronic brake;
    a piston comprising a depressable knob, a shaft in communication with the knob, and a head in communication with the shaft, the shaft and the head movable within the piston housing and medical chamber; and
    an electronic circuit controlling the electronic brake housed in the piston housing,
        wherein the knob of the piston rests outside of the piston housing;

wherein the coupling tabs of the medical chamber engages the retaining slots inside the interior cavity of the piston housing to couple the medical chamber to the piston housing;
wherein the electronic brake engages the piston,
wherein the electronic circuit holds in memory a pre-set of programmable commands that activate or deactivate the electronic brake,
wherein activation of the electronic brake prevents movement of the shaft and the head of the plunger when a user presses on the knob, and
wherein deactivation of the electronic brake allows movement of the shaft and the head of the plunger when the user presses on the knob to dispense the predefined dosage.

2. The injection pen of claim 1, wherein the electronic circuit is configured to control activation or deactivation of the electronic brake such that the predefined dose of the injectable substance is dispensable from the medicinal chamber according to a predefined schedule.

3. The injection pen of claim 2, further comprising a programmable port, wherein the electronic circuit is programmed with one or both of the predefined dose and the predefined schedule by a remote device coupled to the programmable port.

4. The injection pen of claim 1, wherein the electronic circuit is configured to deactivate the electronic brake in response to receiving a pass code from a remote device.

5. The injection pen of claim 1, further comprising a display panel configured to display information related to one or more of a predefined dose of the injectable substance, a predefined schedule of the injectable substance, a battery status of the injection pen, and a network connection status.

6. The injection pen of claim 1, further comprising:
a battery configured to supply power to the electronic circuit; and
a charging terminal including an interface configured to couple with a power source.

7. An injection pen for injecting a substance of a predefined dose to a patient, the injection pen comprising:
a medical chamber substantially cylindrically shaped comprising at least one sidewall extending from an open distal end to a substantially closed proximal end, and defining an internal cavity, the medical chamber including a pair of coupling tabs extending outwardly from a distal peripheral edge of the distal end of the sidewall;
a medical vial insertable into the internal cavity of the medical chamber through the open distal end;
a needle selectively attachable to the closed proximal end of the medical chamber;
a removable cap defining an internal space;
a reservoir disposed inside of the internal space of the removable cap for storing a dispensable solution,
wherein the dispensable solution is dispensed through a dispensing opening included on the reservoir that is disposed in the removable cap;
a piston housing comprising at least one sidewall extending from a proximal open end and a distal end, the piston housing having an interior cavity, retaining slots in the cavity, and an electronic housing at an exterior of the piston housing;
an electronic brake;
a piston comprising a depressable knob, a shaft in communication with the knob, and a head in communication with the shaft, the shaft and the head movable within the piston housing and medical chamber; and
an electronic circuit controlling the electronic brake, the electronic circuit housed inside of the electronic housing,
wherein the electronic circuit is configured to receive a predefined dosage schedule, and control dispensing a predefined dosage as defined by the predefined dosage schedule;
wherein the knob of the piston rests outside of the piston housing;
wherein the coupling tabs of the medical chamber engages the retaining slots inside the interior cavity of the piston housing to couple the medical chamber to the piston housing;
wherein the electronic brake engages the piston,
wherein the electronic circuit holds in memory a pre-set of programmable commands that activate or deactivate the electronic brake,
wherein activation of the electronic brake restricts movement of the shaft and the head of the plunger when a user presses on the knob, and
wherein deactivation of the electronic brake allows movement of the shaft and the head of the plunger when the user presses on the knob to dispense the predefined dosage.

8. The injection pen of claim 7, wherein the solution includes an alcohol-based solution that prepares an injection site on a user body for injecting the injectable substance.

9. The injection pen of claim 7, wherein, after activation of the electronic brake locks the piston, the electronic controller is configured to deactivate the electronic brake allowing movement of the piston in response to receiving a pass code.

10. An injection pen for injecting a substance of a predefined dose to a patient, the injection pen comprising:
a medical chamber substantially cylindrically shaped comprising at least one sidewall extending from an open distal end to a substantially closed proximal end, and defining an internal cavity, the medical chamber including a pair of coupling tabs extending outwardly from a distal peripheral edge of the distal end of the sidewall;
a medical vial insertable into the internal cavity of the medical chamber through the open distal end;
a needle selectively attachable to the closed proximal end of the medical chamber;
a removable cap defining an internal space;
a reservoir disposed inside of the internal space of the removable cap for storing a dispensable solution,
wherein the dispensable solution is dispensed through a dispensing opening included on the reservoir that is disposed in the removable cap;
a piston housing comprising at least one sidewall extending from a proximal open end and a distal end, the piston housing having an interior cavity, retaining slots in the cavity, and an electronic housing at an exterior of the piston housing;
an electronic brake;
a piston comprising a depressable knob, a shaft in communication with the knob, and a head in communication with the shaft, the shaft and the head movable within the piston housing and medical chamber; and
an electronic circuit controlling the electronic brake, the electronic circuit housed inside of the electronic housing and having a programmable port, a display panel configured to display information related to one or more of a predefined dosage of an injectable substance in the medical vial, a predefined schedule of the injectable substance, a battery status of the injection pen, and a network connection status, wherein the electronic circuit is programmable by a remote device coupled to the programmable port, wherein the electronic circuit controls dispensing of the predefined dosage as defined by the predefined dosage schedule by activating or deactivating the electronic brake;

wherein the knob of the piston rests outside of the piston housing;

wherein the coupling tabs of the medical chamber engages the retaining slots inside the interior cavity of the piston housing to couple the medical chamber to the piston housing;

wherein the electronic brake engages the piston, wherein the electronic circuit holds in memory a pre-set of programmable commands that activate or deactivate the electronic brake, wherein activation of the electronic brake restricts movement of the shaft and the head of the plunger when a user presses on the knob, and wherein deactivation of the electronic brake allows movement of the shaft and the head of the plunger when the user presses on the knob to dispense the predefined dosage.

* * * * *